(12) United States Patent
Sekitani et al.

(10) Patent No.: US 11,786,162 B2
(45) Date of Patent: Oct. 17, 2023

(54) ELECTRODE SHEET

(71) Applicants: OSAKA UNIVERSITY, Suita (JP); NIPPON MEKTRON, LTD., Tokyo (JP)

(72) Inventors: Tsuyoshi Sekitani, Suita (JP); Takafumi Uemura, Suita (JP); Teppei Araki, Suita (JP); Shusuke Yoshimoto, Suita (JP); Masayuki Iwase, Tokyo (JP); Akio Yoshida, Tokyo (JP); Hideki Satake, Tokyo (JP)

(73) Assignees: Osaka University, Suita (JP); Nippon Mektron, Ltd., Tokyo (JP)

( * ) Notice: Subject to any disclaimer, the term of this patent is extended or adjusted under 35 U.S.C. 154(b) by 663 days.

(21) Appl. No.: 16/332,723

(22) PCT Filed: Aug. 17, 2017

(86) PCT No.: PCT/JP2017/029555
§ 371 (c)(1),
(2) Date: Mar. 12, 2019

(87) PCT Pub. No.: WO2018/051717
PCT Pub. Date: Mar. 22, 2018

(65) Prior Publication Data
US 2019/0216352 A1    Jul. 18, 2019

(30) Foreign Application Priority Data

Sep. 13, 2016 (JP) .................................. 2016-178924

(51) Int. Cl.
*A61B 5/24* (2021.01)
*A61B 5/05* (2021.01)
(Continued)

(52) U.S. Cl.
CPC .............. *A61B 5/291* (2021.01); *A61B 5/282* (2021.01); *A61B 2562/0215* (2017.08); *A61B 2562/164* (2013.01)

(58) Field of Classification Search
CPC ......... A61B 5/282; A61B 5/259; A61B 5/291; A61B 2562/046; A61B 2562/164;
(Continued)

(56) References Cited

U.S. PATENT DOCUMENTS 5,772,591 A    6/1998 Cram
5,851,438 A    12/1998 Chan
(Continued)

FOREIGN PATENT DOCUMENTS

| JP | H11-232930 A | 8/1999 |
| JP | 2013-121489 A | 6/2013 |
| JP | 2013-132440 A | 7/2013 |
| TW | M524692 U | 7/2016 |
| WO | WO 2005/041768 A1 | 5/2005 |

OTHER PUBLICATIONS

Extended European Search Report issued in European Patent Application No. EP17850623.4 dated Jul. 31, 2019.

*Primary Examiner* — Joseph A Stoklosa
*Assistant Examiner* — Brian M Antiskay
(74) *Attorney, Agent, or Firm* — Knobbe, Martens, Olson & Bear, LLP

(57) ABSTRACT

Provided is an electrode sheet allowing easy connection of a wiring that is extended, when required, to a measurement position on a living body. The electrode sheet (main sheet (1), auxiliary sheet (10)) includes a sheet-shaped flexible substrate (2, 11), wirings (3, 12) formed on the flexible substrate (2, 11), electrodes (5, 14) formed on the flexible substrate (2, 11) and electrically connected to the wirings (3, 12), and an insulating layer (4, 13) laid on the flexible substrate (2, 11) in such a manner that the wirings (3, 12) are overlaid with the insulating layer (4, 13) while the electrodes
(Continued)

(5, 14) are exposed. The electrodes (5, 14) are formed of a conductive material in which conductive particles are dispersed in a thermoplastic resin.

7 Claims, 5 Drawing Sheets

(51) Int. Cl.
*A61B 5/291* (2021.01)
*A61B 5/282* (2021.01)

(58) Field of Classification Search
CPC ... A61B 5/296; A61B 2560/0412; A61B 5/25; A61B 5/0006; A61B 5/6814; A61B 5/68335; A61B 5/6804; A61B 5/6823; A61B 5/6833; A61B 5/6805; A61B 5/6831; A61B 5/389
USPC .......... 600/372, 382–395, 544–545
See application file for complete search history.

(56) References Cited

U.S. PATENT DOCUMENTS

| | | | |
|---|---|---|---|
| 8,934,965 B2* | 1/2015 | Rogers | A61B 5/7246 600/544 |
| 2002/0095080 A1* | 7/2002 | Cory | A61B 5/0531 600/393 |
| 2004/0176674 A1* | 9/2004 | Nazeri | A61B 5/061 600/382 |
| 2006/0074460 A1* | 4/2006 | Maghribi | A61N 1/0543 607/53 |
| 2007/0184682 A1 | 8/2007 | Gobron | |
| 2007/0299471 A1 | 12/2007 | Takahashi et al. | |
| 2011/0237921 A1 | 9/2011 | Askin, III | |
| 2014/0066740 A1* | 3/2014 | Taranekar | A61B 5/25 600/388 |
| 2015/0238106 A1* | 8/2015 | Lappalainen | A61B 5/398 600/383 |
| 2015/0359485 A1* | 12/2015 | Berg | A61B 5/6804 600/388 |
| 2017/0231520 A1* | 8/2017 | Yang | A61B 5/259 600/392 |

* cited by examiner

ELECTRODE SHEET

TECHNICAL FIELD

The present invention relates to an electrode sheet.

BACKGROUND ART

A simple electroencephalograph has been known conventionally, in which an electrode and measuring instrument are integrated. Such a simple electroencephalograph puts a non-negligible burden on a patient, caused by long period measurement by use of a hard electrode. Further, it is difficult for such an electroencephalograph including a fixed electrode to acquire a biological signal meeting the desires of a patient or a doctor. Such a simple electroencephalograph requires a fixing tool such as a head set for fixing the electroencephalograph on the head.

An electrode sheet allowing measurement of a brain wave is proposed as a device enabling more easy measurement of a brain wave, in which three electrodes are disposed on a resin sheet which is attachable to the forehead and has stretchability (refer to Patent Document 1, as an example). According to the proposed electrode sheet, the resin sheet is just attached to the forehead, and thereby a brain wave can be acquired. Accordingly, the electrode sheet enables to reduce the burden on a patient during the long period measurement.

Patent Document 1: Japanese Unexamined Patent Application, Publication No. 2013-121489

DISCLOSURE OF THE INVENTION

Problems to be Solved by the Invention

However, the electrodes of the proposed electrode sheet are fixed to the resin sheet, and thus the proposed electrode sheet allows the acquisition only of brain waves (biological signals) of a living body corresponding to the positions where the three electrodes are formed. Therefore, it is difficult for the proposed electrode sheet to acquire a biological signal at a measurement position away from the positions where the three electrodes are formed and at a position on a living body where the electrode sheet is difficult to be attached. An ideal electrode sheet allows easy connection of a wiring that is extended, when required, to a measurement position on a living body.

The object of the present invention is to provide an electrode sheet allowing easy connection of a wiring that is extended, when required, to a measurement position on a living body.

Means for Solving the Problems

The present invention relates to an electrode sheet which includes a sheet-shaped flexible substrate, a wiring formed on the flexible substrate, an electrode formed on the flexible substrate and electrically connected to the wiring, and an insulating layer laid on the wiring and also laid on the flexible substrate so as to expose the electrode. The electrode is formed of a conductive material in which conductive particles are dispersed in a thermoplastic resin.

A plurality of the electrodes are preferably formed at positions that do not overlap with each other.

The electrodes are preferably formed on both parts, divided by the wiring, of the flexible substrate.

The flexible substrate, the wiring, the electrode and the insulating layer are preferably formed of a stretchable material.

The electrode is preferably formed as a thinner layer than the insulating layer.

Effects of the Invention

The present invention enables to provide an electrode sheet allowing easy connection of a wiring that is extended, when required, to a measurement position on a living body.

PREFERRED MODE FOR CARRYING OUT THE INVENTION

An embodiment of an electrode sheet according to the present invention will be described below with reference to FIG. 1 to FIG. 7. The electrode sheet according to the present embodiment is used to acquire a brain wave, by being attached to, for example, the forehead of a human body. The entirety of the electrode sheet has stretchability and flexibility, and is able to be curved so as to follow the curved shape of the forehead. Accordingly, the electrode sheet can be brought into tight contact with the forehead, thereby enabling to effectively acquire a brain wave.

When used in combination with another electrode sheet, the electrode sheet allows the acquisition of another biological signal in addition to a brain wave. In an example, another electrode sheet is brought into contact with the ear, whereby the earth potential with respect to the brain wave can be acquired. In another example, other electrode sheets are brought into contact with the temple parts (the vicinities of the temples) on the sides of the both eyes, whereby ocular potential can be acquired. It is noted that in the present embodiment, an electrode sheet allowing the acquisition of a brain wave is described as a main sheet 1, while another electrode sheet is described as an auxiliary sheet 10, in order to facilitate understanding. Both of the main sheet 1 and the auxiliary sheet 10 are indicated as one embodiment of the electrode sheet according to the present invention.

Figure 1:
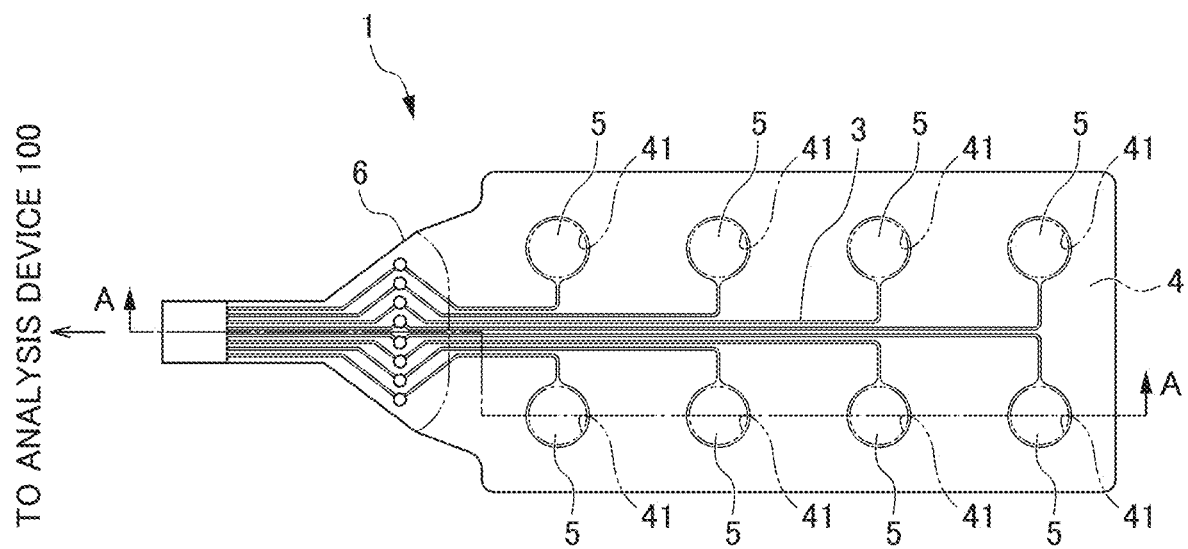
FIG. 1 is a plan view illustrating an electrode sheet according to one embodiment of the present invention.
Figure 2:
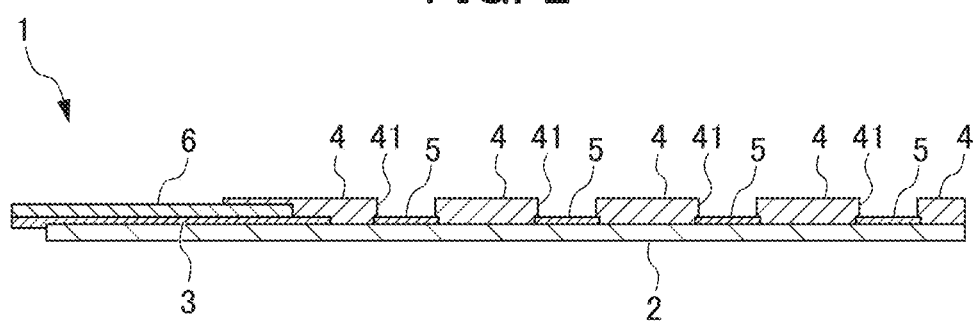
FIG. 2 is a cross-sectional view cut along a line II-II of FIG. 1.

As shown in FIG. 1 and FIG. 2, the main sheet 1 as described above includes a flexible substrate 2, a wiring 3, an electrode 5, an insulating layer 4, and a film base 6. The flexible substrate 2 is formed of, for example, an elastomer material represented by urethane elastomers, into a sheet shape. The flexible substrate 2 has a rectangular shape in a plan view, having one side thereof protruding in an out-of-plane direction. The protruding side of the flexible substrate 2 allows for connection to an external analysis device 100 or radio equipment (not shown) for wirelessly transmitting a biological signal to the analysis device 100. The flexible substrate 2 as described above has stretchability, and extends in an in-plane direction by an external force.

The wiring 3 is formed of a conductive material in which conductive particles are dispersed in a resin material (resin binder). The wiring 3 is linearly formed so as to traverse across the flexible substrate 2. Specifically, the wiring 3 is formed so as to traverse within the plane of the flexible substrate 2 from the protruding side of the flexible substrate 2 to the opposing side. In the present embodiment, eight wirings 3 are disposed. The conductive material itself of the wirings 3 has a very low Young's modulus (for example, 100 MPa or lower, more preferably 10 MPa or lower), and thus each of the wirings 3 exhibits a behavior of following the expanding and contracting motion in an in-plane direction of the flexible substrate 2. The wirings 3 can be formed by, for example, a printing method.

The electrodes 5 are formed of a conductive material in which conductive particles are dispersed in a thermoplastic resin (resin binder). Each of the electrodes 5 as described above is formed to have a circular shape in a plan view on the flexible substrate 2, and is electrically connected to the wiring 3. In the present embodiment, four electrodes 5 are formed on each of the both parts, divided by the wirings 3, on the same plane of the flexible substrate 2. The electrodes 5 are formed at positions that do not overlap with each other. Each of the electrodes 5 has a low Young's modulus (for example, 100 MPa or lower, more preferably 10 MPa or lower) as with the wirings 3, and exhibits high followability with respect to the movement of the flexible substrate 2. The electrodes 5 can be formed by a printing method together with the formation of the wirings 3, as an example.

The insulating layer 4, which is a stretchable sheet-shaped cover formed of, for example, an elastomer material, is laid on the wirings 3. In the present embodiment, the insulating layer 4 is formed so as to be laid on the flexible substrate 2, while covering the positions where the wirings 3 are formed. In particular, the insulating layer 4 is formed so as to be laid on the rectangular region of the flexible substrate 2 and a part of the region formed with the protruding side. The insulating layer 4 has through holes 41 each which has a diameter smaller than the diameter of the electrodes 5, at the positions corresponding to the electrodes 5. Accordingly, the electrodes 5 are exposed by the through holes 41.

The film base 6 is formed in correspondence with the shape of the region formed with the protruding side of the flexible substrate 2, and is laid on the wirings 3 and the surface of the flexible substrate 2. The film base 6 is formed of a material having higher in-plane rigidity than that of the flexible substrate 2, thereby preventing the wirings 3 from disconnecting. The film base 6 also has moderate stiffness, and thus enables to improve the handling properties when the analysis device 100 not shown and the electrode sheet (the main sheet 1) are connected.

Hydrogel or a conductive adhesive (not shown) is applied on the surfaces exposed under the insulating layer 4, of the main sheet 1 as described above, and the main sheet 1 is attached to an arbitrary measurement position (for example, the forehead) on a living body. Since each of the flexible substrate 2, the wirings 3, the electrodes 5 and the insulating layer 4 have stretchability, the main sheet 1 comes into tight contact with a living body in a curved state following the shape of the living body. Accordingly, the electrodes 5 come into tight contact with the living body, whereby the electrodes 5 are able to acquire biological signals at the tight contact positions. On the other hand, the wirings 3 are formed so as not to come into contact with the living body due to the insulating layer 4, thereby preventing the acquisition of unintended biological signals through the wirings 3. That is, such configuration enables to prevent noise from being added to the biological signals acquired by the electrodes 5. The film base 6 having high in-plane rigidity is able to protect the wirings 3 disposed in the region formed by the protruding side of the flexible substrate 2, thereby enabling to protect the wirings 3 from disconnection.

Figure 3:
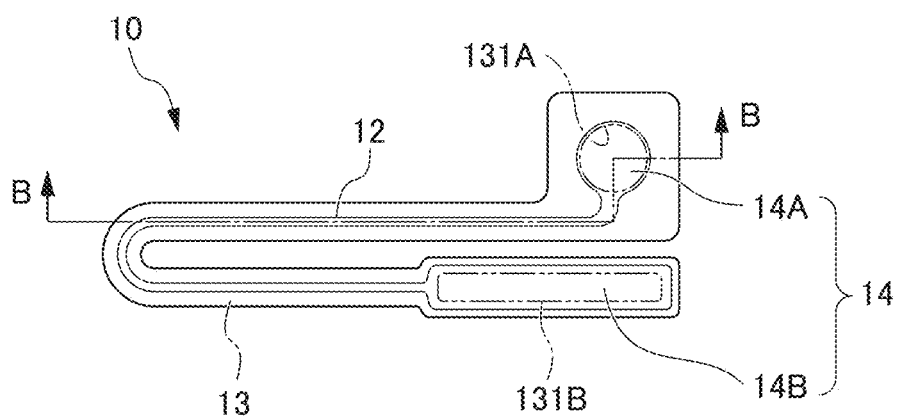
FIG. 3 is a plan view illustrating another electrode sheet according to the one embodiment.
Figure 4:
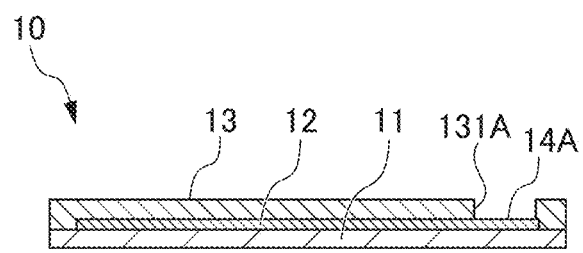
FIG. 4 is a sectional view cut along a line IV-IV of FIG. 3.

The auxiliary sheet 10 is described below with reference to FIG. 3 and FIG. 4. As shown in FIG. 3 and FIG. 4, the auxiliary sheet 10 includes a flexible substrate 11, a wiring 12, an electrode 14, and an insulating layer 13.

The flexible substrate 11 is formed of, for example, an elastomer material represented by urethane elastomers, into a sheet shape. The flexible substrate 11 is formed to have a linear shape, and is formed in a folded-back shape in which the middle portion thereof is curved in the same plane. The both ends of the flexible substrate 11 are formed to be expanded in the width direction. The flexible substrate 11 has stretchability, and extends in an in-plane direction by an external force.

The wiring 12 is formed of a conductive material in which conductive particles are dispersed in a resin material (resin binder). The wiring 12 is formed linearly along the flexible substrate 11. Specifically, the wiring 12 is formed linearly at the center in the width direction of the flexible substrate 11. The conductive material itself of the wiring 12 has a very low Young's modulus (for example, 100 MPa or lower, more preferably 10 MPa or lower), and thus the wiring 12 exhibits a behavior of following the expanding and contracting motion in an in-plane direction of the flexible substrate 11. The wiring 12 can be formed by, for example, a printing method.

The electrode 14 is formed of a conductive material in which conductive particles are dispersed in a thermoplastic resin (resin binder). The electrode 14 as described above includes a circular electrode 14A formed on one end side of the flexible substrate 11 and a rectangular electrode 14B formed on the other end side. The circular electrode 14A is formed to have a circular shape in a plan view, and is electrically connected to one end of the wiring 12. The circular electrode 14A has a low Young's modulus (for example, 100 MPa or lower, more preferably 10 MPa or lower) as with the wiring 12, and exhibits high followability with respect to the movement of the flexible substrate 11. The circular electrode 14A can be formed by a printing method together with the formation of the wiring 12, as an example. The rectangular electrode 14B is formed to have a rectangular shape in a plan view, and is electrically connected to the other end of the wiring 12. The rectangular electrode 14B has a low Young's modulus (for example, 100 MPa or lower, more preferably 10 MPa or lower) as with the wiring 12 and the circular electrode 14A having stretchability as with the flexible substrate 11, the wiring 12 and the circular electrode 14A, and exhibits high followability with respect to the movement of the flexible substrate 11. The rectangular electrode 14B can be formed by a printing method together with the formation of the wiring 12 and the circular electrode 14A, as an example.

The insulating layer 13, which is a stretchable sheet-shaped cover formed of, for example, an elastomer material, is laid on the wiring 12. In the present embodiment, the insulating layer 13 is formed so as to be laid on the flexible substrate 11, while covering the position where the wiring 12 is formed. In particular, the insulating layer 13 is formed in correspondence with the shape of the flexible substrate 11.

The insulating layer 13 has a through hole 131A which has a diameter smaller than the diameter of the circular electrode 14A at the position corresponding to the circular electrode 14A. Accordingly, the circular electrode 14A is exposed by the through hole 131A. The insulating layer 13 further has a rectangular through hole 131B which has a smaller opening area than the area of the rectangular electrode 14B at the position corresponding to the rectangular electrode 14B. Accordingly, the rectangular electrode 14B is exposed by the through hole 131B.

Hydrogel or a conductive adhesive (not shown) is applied on the surface of the rectangular electrode 14B on the auxiliary sheet 10 as described above, and thus the rectangular electrode 14B can be attached to an arbitrary measurement position (for example, the ear or the eyelid) on a living body. Since each of the flexible substrate 11, the rectangular electrode 14B and the insulating layer 13 have stretchability, the rectangular electrode 14B can come into tight contact with a living body in a curved state following the shape of the living body.

According to the main sheet 1 and the auxiliary sheet 10 as described above, as shown in FIG. 5 and FIG. 6, the flexible substrate 2, the electrodes 5 and the insulating layer 4 included in the main sheet 1, and the flexible substrate 11, the circular electrode 14A and the insulating layer 13 included in the auxiliary sheet 10 are each formed of a thermoplastic resin. Therefore, the both sheets are laid on each other and then subjected to thermal compression bonding, thereby allowing easy bonding. As a result, the wiring 3 of the main sheet 1 and the wiring 12 of the auxiliary sheet 10 are electrically connected, and hence the biological signal acquired by the rectangular electrode 14B of the auxiliary sheet 10 can be transmitted to the electrode 5 of the main sheet 1, via the wiring 12 and the circular electrode 14A. In particular, the electrode 5 and the circular electrode 14A are bonded to each other so that their exposed surfaces are opposed to each other (the insulating layer 4 and the insulating layer 13 are opposed to each other). Therefore, when the main sheet 1 is attached to the living body, the flexible substrate 11 of the auxiliary sheet 10 comes into contact with the living body. This method enables to prevent a biological signal from being disadvantageously acquired from the position of the bonded electrode 5, and therefore noise can be prevented from being added to a biological signal. It is noted that although the wiring 12 and the rectangular electrode 14B of the auxiliary sheet 10 are indicated by solid lines in FIG. 5, the both are positioned on the back side of the flexible substrate 11. Furthermore, although the through hole 131B is indicated by a two-dot chain line in FIG. 5, the through hole 131B is positioned on the back side of the flexible substrate 11.

Figure 5:
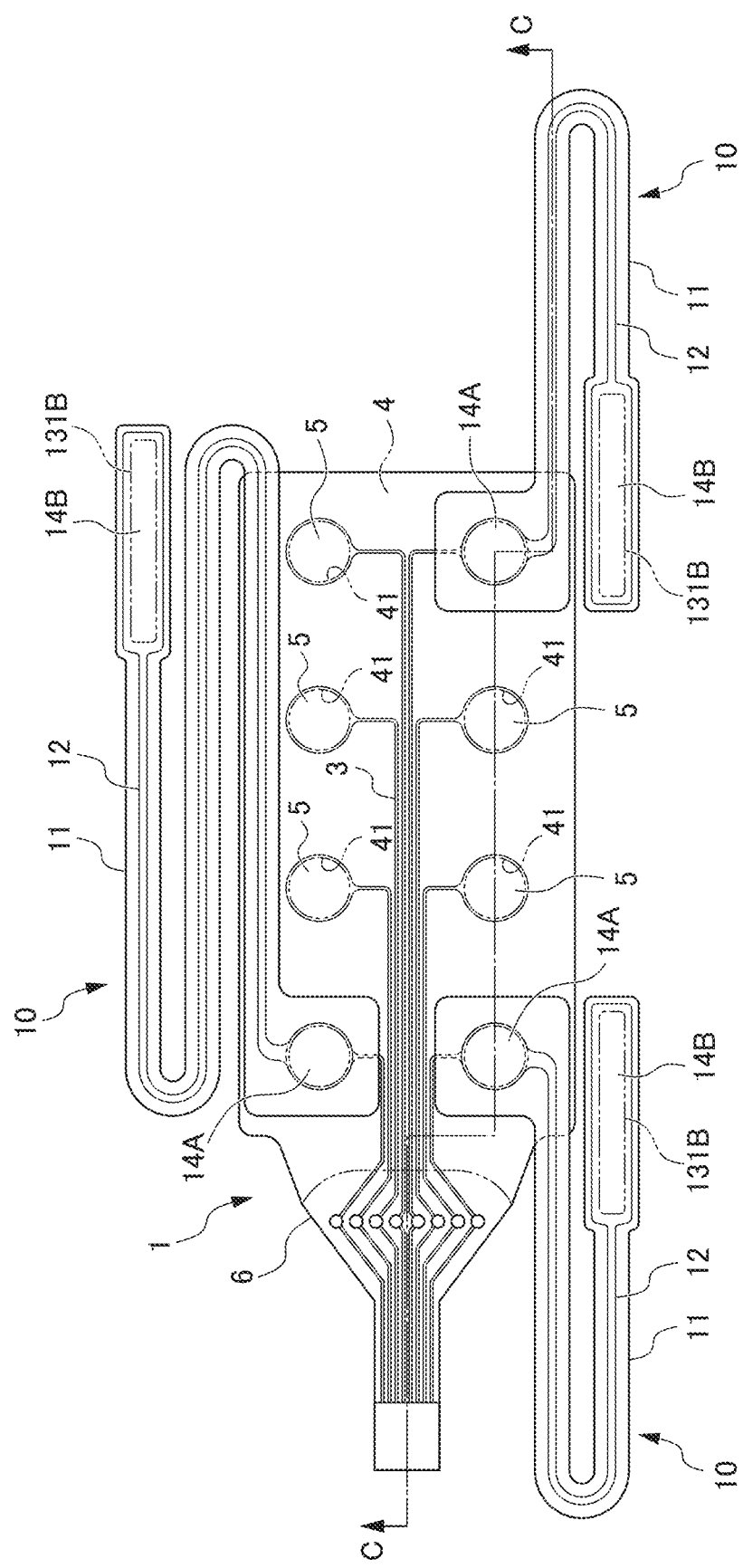
FIG. 5 is a plan view of the electrode sheet according to the one embodiment after other electrode sheets are pressure-bonded thereto.
Figure 6:
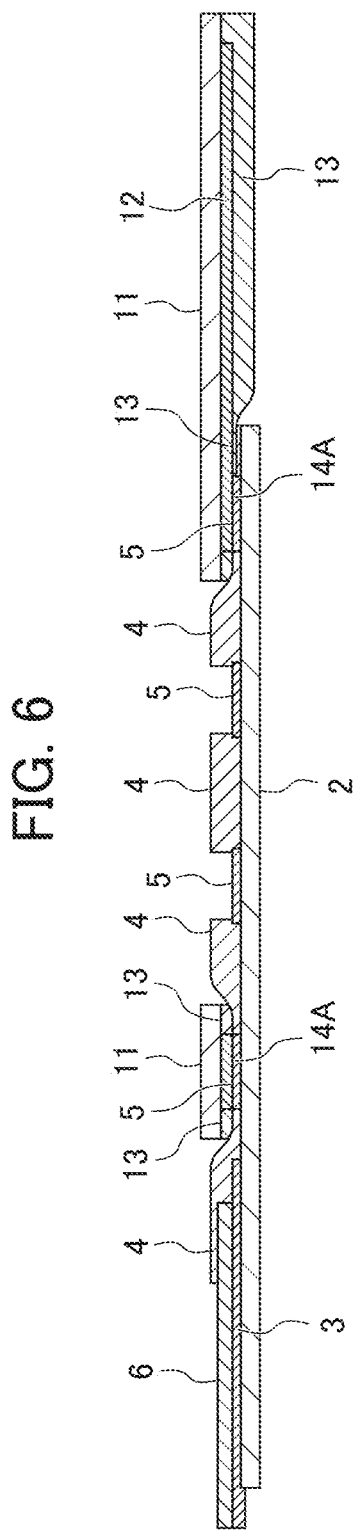
FIG. 6 is a sectional view cut along a line VI-VI of FIG. 5.
Figure 7:
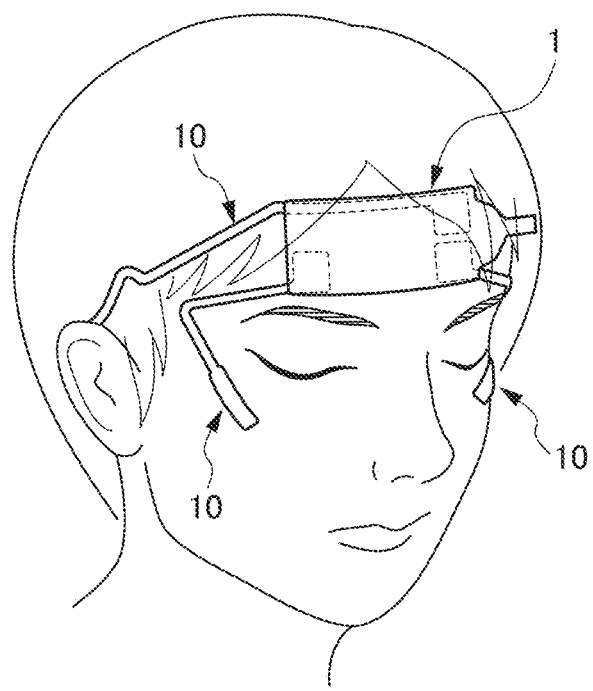
FIG. 7 is a plan view illustrating an example of use of the electrode sheet illustrated in FIG. 5.

Since each of the flexible substrate 11, the wiring 12 and the insulating layer 13 of the auxiliary sheet 10 have stretchability, the flexible substrate 11, the wiring 12 and the insulating layer 13 can extend according to the distance from the position where the circular electrode 14A is bonded, to a measurement position. In particular, the main sheet 1 has four electrodes 5 on each of the both parts divided by the wirings 3. Accordingly, the electrode 5 to be subjected to bonding can be selected among the electrodes 5 on the basis of the measurement position, whereby the main sheet 1 and the auxiliary sheet 10 can be connected so that the wiring 12 of the auxiliary sheet 10 does not cause any disturbance, nor is excessively extended. In the present embodiment, as shown in FIG. 5 and FIG. 7, the circular electrodes 14A of the auxiliary sheets 10 are connected to each of three electrodes 5 of the main sheet 1, and each of the auxiliary sheets 10 are able to input biological signals of one of the ears and each of the temple parts (the vicinities of the temples) on the sides of the both eyes, to the main sheet 1. In particular, the main sheet 1 and the auxiliary sheets 10 are provided to a user as individual sheets, and thus the auxiliary sheets 10 allow easy and selective connection, when required, to the electrodes 5 of the main sheet 1 by thermal compression bonding. Accordingly, the convenience for the user is greatly improved.

The electrode sheets as described above are used as follows. First, for one main sheet 1 for acquiring a brain wave from the forehead, the number of auxiliary sheets 10 corresponding to the number of other measurement positions are prepared. In the present embodiment, three auxiliary sheets 10 are prepared in order to acquire respective biological signals of one of the ears and each of the temple parts (the vicinities of the temples) on the sides of the both eyes.

Each of the circular electrodes 14A of the three auxiliary sheets 10 is exclusively bonded to any one of the electrodes 5 of the main sheet 1. Specifically, each of the circular electrodes 14A of the three auxiliary sheets 10 is bonded to any one of the electrodes 5 of the main sheet 1 by thermal compression bonding, whereby the circular electrodes 14A of the auxiliary sheets 10 are bonded in a mutually exclusive state. In the present embodiment, the auxiliary sheet 10 for acquiring a biological signal of one of the ears is bonded to the electrode 5 which is positioned closest to the protruding side among the electrodes 5 positioned on one of the parts divided by the wirings 3, of the main sheet 1. Then, each of the auxiliary sheets 10 for acquiring biological signals of each of the temple parts (the vicinities of the temples) on the sides of the both eyes are bonded to the electrode 5 which is positioned closest to the protruding side and the electrode 5 which is positioned farthest from the protruding side, among the electrodes 5 disposed on the other part divided by the wirings 3, of the main sheet 1.

After the main sheet 1 is attached to the forehead, each of the auxiliary sheets 10 is attached to each of the measurement positions, as shown in FIG. 7, whereby respective biological signals are acquired. The electrodes 5 which are not bonded to the auxiliary sheets 10 among the electrodes 5 of the main sheet 1 acquire brain waves of the living body, and transmit the biological signals to the analysis device 100 via the wirings 3. The electrodes 5 connected to the auxiliary sheets 10 acquire the biological signals acquired by the electrodes 14 of the auxiliary sheets 10, and transmit the biological signals to the analysis device 100 via the wirings 3. As a result, not only brain waves but also other biological signals can be transmitted to the analysis device 100.

The electrode sheets according to the embodiment described above exert the following effects.

(1) Each of the electrode sheets (the main sheet 1, the auxiliary sheet 10) are configured with the sheet-shaped flexible substrates 2, 11, the wirings 3, 12 respectively formed on the flexible substrates 2, 11, the electrodes 5, 14 respectively formed on the flexible substrates 2, 11 and electrically connected to the wirings 3, 12, and the insulating layers 4, 13 respectively laid on the wirings 3, 12 and on the regions excluding the portions where the electrodes 5, 14 are formed, in the regions on the flexible substrates 2, 11. The electrodes 5, 14 are formed of a conductive material in which conductive particles are dispersed in a thermoplastic resin. Accordingly, when the electrode sheets (the main sheet 1, the auxiliary sheet 10) are brought into contact with a human body via biocompatible hydrogel or a biocompatible conductive adhesive, biological signals of a human body can be acquired by use of the electrodes 5, 14. On the other hand, since the insulating layers 4, 13 are formed by being laid on the wirings 3, 12 respectively, the wirings 3, 12 do not come into contact with the human body. The noise generated when the wirings 3, 12 acquire biological signals can be eliminated, and accordingly biological signals with higher accuracy can be acquired. The electrodes 5, 14 of the plurality of electrode sheets (the main sheet 1, the auxiliary sheets 10) can be bonded by thermal compression bonding after the electrodes 5, 14 are laid on each other. Therefore, a material for bonding such as ACF (Anisotropic Conductive Film) is not required, and thus the electrode sheets allow easy connection of the wirings 3, 12 which are extended, when required, to the measurement positions on a living body. Accordingly, biological signals can be acquired by use of the wirings 3, 12 extended to the measurement positions on a living body, via the wirings 3, 12 of another electrode sheet (the auxiliary sheet 10).

(2) The plurality of electrodes 5 are formed at positions that do not overlap with each other. Therefore, each of the electrodes 5 is able to acquire a biological signal. At least one of the electrodes 5 is bonded by thermal compression bonding to the electrode 14 of another electrode sheet (the auxiliary sheet 10), whereby the at least one of the electrodes 5 subjected to the thermal compression bonding receive the biological signal acquired at another position, while the other electrodes 5 not subjected to the thermal compression bonding acquire biological signals. Accordingly, more biological signals can be acquired without being influenced by the positions where the electrodes 5 are formed.

(3) The electrodes 5 are formed on the both parts, divided by the wirings 3, of the flexible substrate 2. Accordingly, in the case where the electrode 14 of another electrode sheet (the auxiliary sheet 10) is to be bonded by thermal compression bonding, the electrode 5 which is positioned close to the measurement position where a biological signal is to be acquired by another electrode sheet (the auxiliary sheet 10) can be selected and subjected to the thermal compression bonding to the electrode 14. A different electrode 5 may be selected and subjected to the thermal compression bonding according to the measurement position of a biological signal, thereby enabling to improve the convenience in the electrode sheets (the main sheet 1, the auxiliary sheet 10).

(4) The flexible substrates 2, 11, the wirings 3, 12, the electrodes 5, 14 and the insulating layers 4, 13 are formed of a stretchable material (including a concept in which a part of the constituent material has a low Young's modulus (for example, 100 MPa or lower, more preferably 10 MPa or lower)). As a result, the electrode sheets (the main sheet 1, the auxiliary sheet 10) are able to be curved so as to follow the curved shape of a living body, thereby enabling to acquire excellent biological signals under the state of being in tight contact with the living body.

(5) The electrodes 5, 14 are formed as thinner layers than the insulating layers 4, 13. Therefore, even in the case where the electrodes 5, 14 formed of a thermoplastic resin are softened by heating, the electrodes 5, 14 can be bonded to each other without overflowing on the surfaces of the insulating layers 4, 13.

The preferred embodiment of the electrode sheet according to the present invention has been described so far. The present invention is not limited to the above-described embodiment. Other embodiments modified appropriately are available. For example, each of the flexible substrates 2, 11 is formed to have a thickness of, for example, 100 μm or less, more preferably 25 μm or less, further preferably 10 μm or less, from the viewpoint that the flexible substrates 2, 11 attached to a living body are not to inhibit the movement of the living body. The flexible substrates 2, 11 as described above have the maximum elongation rate of, more preferably 50% or more, especially preferably 500% or more. The maximum elongation rate herein of the flexible substrates 2, 11 means the maximum value of the elongation rate by which the flexible substrates 2, 11 are elastically deformable in one direction along an in-plane direction. The elongation rate herein of the flexible substrates 2, 11 means the rate of elongation in one direction along an in-plane direction when a force is applied, with respect to the dimension when no external force is applied (the dimension under the elongation rate of 0%). In an example, in the case where the elongation rate is 50%, the elongation rate is 1.5 times the dimension under the elongation rate of 0%. In the case where the elongation rate is 500%, the elongation rate is 5 times the dimension under the elongation rate of 0%. Each of the flexible substrates 2, 11 as described above has a Young's modulus of approx. 7 MPa.

The wirings 3, 12 and the electrodes 5, 14 can be formed by selective use of a material excellent in conductivity, such as silver, gold, platinum, carbon, copper, aluminum, cobalt or nickel, or an alloy of these. The present invention is not limited to a specific shape of such a conductive material. Such a conductive material may be of granular particles, powder particles or the like. The present invention is not limited to a specific particle shape. Such a particle shape may be a spherical shape, a needle-like shape, a flake-like shape, a nanowire-like shape or the like. The aspect ratio of such particles may be, for example, in a range of 1 or more and 100 or less, in particular of 1 or more and 50 or less. The aspect ratio herein means the ratio of the longest dimension and the shortest dimension of a three-dimensional body. The wirings 3, 12 and the electrodes 5, 14 are formed of the material including the particles having the aspect ratio in a range of 5 or more and 5000 or less (it is noted that the material including the particles having the aspect ratio of approx. 5000 is silver nanowire or the like), thereby enabling to suppress resistivity change in the case where the electrode sheet (the main sheet 1, the auxiliary sheet 10) is extended in an in-plane direction and accordingly the wirings 3, 12 and the electrodes 5, 14 are deformed in the longitudinal direction.

The wirings 3, 12 and the electrodes 5, 14 can be formed by use of an elastomer material of thermoplastic resin, such as urethane resin binder, acrylic resin binder or polyester resin binder, as a resin binder. The resin binder having a low Young's modulus (for example, 100 MPa or lower, more preferably 10 MPa or lower) is preferably selected so that the elastic modulus of the resin binder is equal to or lower than the elastic modulus of the coated wirings 3, 12 and the coated electrodes 5, 14. One type of elastomer material may be used, or alternatively various types of elastomer materials may be mixed and used.

The wirings 3, 12 and the electrodes 5, 14 can be formed by a printing method, for example, a screen printing method, an inkjet printing method, a gravure printing method or an offset printing method. In particular, a screen printing method is preferably used from the viewpoint of fine resolution and stability with thick film. In the case where the wirings 3, 12 and the electrodes 5, 14 are formed by a printing method, a conductive paste containing the conductive particles and the resin binder described above as well as an organic solvent can be prepared and used for the printing method. The usage of a stretchable conductive paste mainly containing metal particles such as silver for the wirings 3, 12 and the electrodes 5, 14 enables to realize the elongation rate of, for example, approx. 50% or more and 70% or less, thereby allowing the formation of the wirings 3, 12 having excellent elongation characteristics.

The dimensions in thickness and the dimensions in width of the wirings 3, 12 and the electrodes 5, 14 can be determined on the basis of not only the resistivities of the wirings 3, 12 and the electrodes 5, 14 in unloaded states and the resistivity change of the electrode sheets (the main sheet 1, the auxiliary sheet 10) in extended states, but also on the basis of the restrictions of the dimensions in thickness and the dimensions in width of the entire electrode sheets (the main sheet 1, the auxiliary sheet 10). In particular, the dimensions in width of the wirings 3, 12 are preferably 1000 µm or less, more preferably 500 µm or less, further preferably 200 µm or less, from the viewpoint that excellent stretchability is secured so that the wirings 3, 12 follow the change in dimensions when the flexible substrates 2, 11 are extended. Each wiring of the wirings 3, 12 included in the wirings 3, 12 may have the dimension in thickness of 25 µm or less, preferably in the range of 10 µm or more and 15 µm or less.

The insulating layers 4, 13 may be formed of the resin material common to the flexible substrates 2, 11. Such formation enables to protect the wirings 3, 12 without spoiling the stretchability of the stretchable regions of the flexible substrates 2, 11. The insulating layers 4, 13 can be formed in such a manner that an elastomer type paste is applied on the film base 6 and the flexible substrates 2, 11 and is then dried. Alternatively, the insulating layers 4, 13 which are formed in advance to have sheet shapes with the through holes 41, 131 may be attached to the film base 6 and the flexible substrates 2, 11, or may be bonded by use of an adhesive having stretchability. The thickness of each of the insulating layers 4, 13 is preferably 100 µm or less, more preferably 50 µm or less, further preferably 30 µm or less, from the viewpoint that the stretchability of the flexible substrates 2, 11 is not to be spoiled due to the thickness.

The film base 6 may have a Young's modulus (for example, 5 to 10 GPa) larger than those of the flexible substrates 2, 11, and may be formed of a synthetic resin having low sliding properties, corrosion resistance and excellent strength, such as polyethylene terephthalate (PET), polyethylene naphthalate (PEN), polyimide (PI) or polyphenylene sulfide (PPS). Alternatively, the film base 6 may be formed by use of a paper material having appropriate durability, such as cellulose nanofiber paper.

In the case where a urethane elastomer sheet is used as the film base 6, the urethane elastomer sheet has thermal adhesiveness, and thus the film base 6 can be bonded by thermal compression bonding, to each of the flexible substrates 2, 11 serving as a bonding object, so as to be integrated in a laminated state. Such direct bonding of the film base 6 and each of the flexible substrates 2, 11 allows the disuse of a material for bonding, such as ACF, and simplifies the bonding process. The film base 6 and each of the flexible substrates 2, 11 are not bonded without heating nor pressure bonding. Accordingly, even in the case of positioning requiring high precision, the positioning can be corrected, and thereby workability is improved. It is noted that the state where two layers are bonded means that the targeted two layers are directly contacted and integrated by a bonding method, such as heat press (thermal compression bonding).

In the above-described embodiment, the main sheet 1 includes eight electrodes 5. The present invention is not limited thereto, and any number of electrodes 5 may be disposed. The present invention is not limited to three auxiliary sheets 10. Any number of the auxiliary sheets 10 may be disposed so as to correspond to the number of the measurement positions. The auxiliary sheets 10 may be connected to each other, so that the wiring 12 is lengthened. In the description above, the main sheet 1 is used as an electrode sheet for acquiring a brain wave. However, the present invention is not limited thereto. The main sheet 1 may be attached to various positions on a living body, as an electrode sheet for acquiring various types of biological signals, such as a blood pressure and a pulse rate.

EXPLANATION OF REFERENCE NUMERALS

1 MAIN SHEET
2, 11 FLEXIBLE SUBSTRATE
3, 12 WIRING
4, 13 INSULATING LAYER
5, 14 ELECTRODE
10 AUXILIARY SHEET

The invention claimed is:

1. An electrode sheet, comprising:
a main sheet; and
an auxiliary sheet,
the main sheet, comprising:
  a sheet-shaped first flexible substrate;
  a first wiring formed on the first flexible substrate;
  a plurality of first electrodes formed on the first flexible substrate and electrically connected to the first wiring; and
  a first insulating layer laid on the first wiring, and also laid on the first flexible substrate so as to expose the plurality of first electrodes,
the auxiliary sheet, comprising:
  a second flexible substrate formed sheet-shaped and linear shape;
  a second wiring formed on the second substrate and linear shape along the second flexible substrate,
  a second electrode formed on the second flexible substrate, said second electrode comprising a first part connected to a first end side of the second wiring and a second part connected to a second end side of the second wiring; and
  a second insulating layer laid on the second wiring, and also laid on the second flexible substrate so as to expose the second electrode,
wherein
  the plurality of first electrodes and the second electrode are formed of a conductive material including conductive particles dispersed in a thermoplastic resin,
  the first part of the second electrode is movable so as to connect to any one of the plurality of first electrodes so that said one of the plurality of first electrodes is selectively connected to the first part of the second electrode and thereby move a position of the second part of the second electrode of the auxiliary sheet on skin of a subject,
  one of the plurality of first electrodes and the first part of the second electrode are exposed, and their exposed surfaces are bonded to each other.

2. The electrode sheet according to claim 1, wherein the plurality of the first electrodes are formed at positions that do not overlap with each other.

3. The electrode sheet according to claim 2, wherein the first flexible substrate has two areas, divided by the first wiring, formed on the same plane,
the first electrodes are formed on each of the two areas, divided by the first wiring, of the first flexible substrate.

4. The electrode sheet according to claim 1, wherein the first flexible substrate, the first wiring, the first electrode and the first insulating layer are formed of a stretchable material.

5. The electrode sheet according to claim 1, wherein the first electrode is formed as a thinner layer than the first insulating layer.

6. The electrode sheet according to claim 1, wherein the first part of the second electrode is a circular electrode.

7. The electrode sheet according to claim 1, wherein the second part of the second electrode is a rectangular electrode.

\* \* \* \* \*